US006853703B2

United States Patent
Svatos et al.

(10) Patent No.: US 6,853,703 B2
(45) Date of Patent: Feb. 8, 2005

(54) AUTOMATED DELIVERY OF TREATMENT FIELDS

(75) Inventors: Michelle Marie Svatos, Oakland, CA (US); William F. Collins, Clayton, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 249 days.

(21) Appl. No.: 09/909,589

(22) Filed: Jul. 20, 2001

(65) Prior Publication Data

US 2003/0191384 A1 Oct. 9, 2003

(51) Int. Cl.$^7$ .............................................. A61N 5/10
(52) U.S. Cl. ....................................... 378/65; 378/69
(58) Field of Search ........................... 378/65, 69, 147, 378/148, 151

(56) References Cited

U.S. PATENT DOCUMENTS

| | | | |
|---|---|---|---|
| 4,220,866 A | | 9/1980 | Taumann et al. |
| 4,726,046 A | | 2/1988 | Nunan |
| 4,880,985 A | | 11/1989 | Jones |
| 5,160,847 A | | 11/1992 | Leavitt et al. |
| 5,396,889 A | | 3/1995 | Ueda et al. |
| 6,167,114 A | | 12/2000 | Siochi |
| 6,222,544 B1 | * | 4/2001 | Tarr et al. .................... 345/839 |
| 6,449,335 B1 | * | 9/2002 | Siochi ......................... 378/65 |
| 6,477,229 B1 | * | 11/2002 | Grosser ....................... 378/65 |

FOREIGN PATENT DOCUMENTS

| | | |
|---|---|---|
| JP | 7116276 A | 5/1995 |
| JP | 11216196 A | 8/1999 |
| JP | 2001276238 A | 10/2001 |
| WO | WO 00/13189 | 3/2000 |

OTHER PUBLICATIONS

Ma et al., "Energy– and intensity–modulated electron beams for radiotherapy" (IOP Publishing Ltd, vol. 45, No. 8, Aug. 1, 2000; pp. 2293–2311).

Karlsson et al. "Treatment head design for multileaf collimated high–energy electrons" (Medical Physics, vol. 26, No. 10, Oct. 1999, pp. 2161–2167).

Moran et al. "Characteristics of scattered electron beams shaped with a multileaf collimator" (Medical Physics, vol. 24, No. 9, Sep. 1997; pp. 1491–1498).

Zhu et al. "Characteristics of bremsstrahlung in electron beams" (Medical Physics, vol. 28, No. 7, Jul. 2001; pp. 1352–1358).

* cited by examiner

Primary Examiner—Louis M. Arana (57) ABSTRACT

A system, method, apparatus, and means for delivering treatment fields includes identifying a sequence group. A type of radiation to be applied in a first field of the sequence group is identified. The type of radiation is selected from among primary photon radiation and primary electron radiation. A radiation therapy treatment device is configured, based at least in part on the type of radiation. The first field is then delivered.

17 Claims, 4 Drawing Sheets

AUTOMATED DELIVERY OF TREATMENT FIELDS

CROSS-REFERENCE TO RELATED APPLICATIONS

This application is related to commonly owned U.S. patent application Ser. No. 09/910,526, filed Jul. 20, 2001 for "VERIFICATION OF ELECTRON TREATMENT FIELDS", and U.S. patent application Ser. No. 09/909,513, filed Jul. 20, 2001, for "REMOVABLE ELECTRON MULTILEAF COLLIMATOR", the contents of each of which are incorporated by reference in their entirety for all purposes.

BACKGROUND OF THE INVENTION

1. Field of the Invention

The present invention relates generally to radiation therapy devices, and more particularly, to the automated delivery of radiation therapy.

2. Description of the Related Art

Conventional radiation therapy typically involves directing a radiation beam at a tumor in a patient to deliver a predetermined dose of therapeutic radiation to the tumor according to an established treatment plan. This is typically accomplished using a radiation therapy device such as the device described in U.S. Pat. No. 5,668,847 issued Sep. 16, 1997 to Hernandez, the contents of which are incorporated herein for all purposes.

The radiotherapy treatment of tumors involves three-dimensional treatment volumes which typically include segments of normal, healthy tissue and organs. Healthy tissue and organs are often in the treatment path of the radiation beam. This complicates treatment, because the healthy tissue and organs must be taken into account when delivering a dose of radiation to the tumor. While there is a need to minimize damage to healthy tissue and organs, there is an equally important need to ensure that the tumor receives an adequately high dose of radiation. Cure rates for many tumors are a sensitive function of the dose they receive. Therefore, it is important to closely match the radiation beam's shape and effects with the shape and volume of the tumor being treated.

Both primary photon and primary electron beams may be used in radiation therapy. Accordingly, many existing radiation therapy devices include the ability to generate and deliver both photon and electron beams. Currently, clinical practice requires substantial manual intervention to use conformal electron treatment. Conformal photon fields typically are shaped using one or more collimating devices positioned between the source and the treatment area. Many of these photon beam collimating devices may be positioned automatically to deliver a desired photon field shape to a treatment area on a patient. Little manual intervention is required to administer photon radiation therapy.

Primary electrons are currently used on approximately 30% of all patients who undergo radiation therapy. Electron fields delivered via radiation therapy devices are typically shaped using either an off-the-shelf electron applicator (either rectangular or circular in cross-section) or a custom cutout formed of Cerrobend®. Both of these beam shaping methods have limitations. Off-the-shelf electron applicators often unnecessarily irradiate portions of healthy tissue, since they do not precisely conform to the target. Custom cutouts formed of Cerrobend® are highly conformal, but are costly to make, store and require special quality assurance. The Cerrobend® material may also require special handling because of the potentially toxic metals involved. Each of these approaches to electron field shaping also suffer in that they can be inefficient to use. A radiation therapist delivering a prescribed treatment must repeatedly enter the treatment room during treatment to insert the proper cutout for each field in the therapy. This is not only inefficient, but it effectively precludes the delivery of treatments which require electron field modulation in both intensity and energy at a single gantry position.

As described in co-pending and commonly assigned U.S. patent application Ser. Nos. 09/910,526, and 09/909,513 (referenced above), Applicants have developed a radiation therapy device, verification approach, and electron collimator which overcome many of these difficulties associated with delivery of both electron and photon beams from a single radiation therapy device.

It would be desirable to provide a system and method for automating the delivery of treatment fields. In particular, it would be desirable to provide a system and method of delivering treatment fields in a radiation therapy device having the ability to deliver both primary photon and primary electron fields.

SUMMARY OF THE INVENTION

To alleviate the problems inherent in the prior art, and to allow the accurate, efficient and effective delivery of photon, electron, and mixed beam radiation therapy, embodiments of the present invention provide a system and method for the automated delivery of treatment fields.

According to one embodiment of the present invention, a system, method, apparatus, and means for delivering treatment fields includes identifying a sequence group. A type of radiation to be applied in a first field of the sequence group is identified. The type of radiation is selected from among primary photon radiation and primary electron radiation. A radiation therapy treatment device is configured, based at least in part on the type of radiation. The first field is then delivered. In some embodiments, a determination is made whether the sequence group is to be applied with radiation or not. A sequence without applied radiation may be performed for testing purposes.

In some embodiments, a sequence group may include a number of fields. For each field, the type of radiation is identified, the radiation therapy device is configured, and the field is delivered. In some embodiments, configuration of the radiation therapy device includes positioning elements of a photon collimator and elements of an electron collimator.

The present invention is not limited to the disclosed preferred embodiments, however, as those skilled in the art can readily adapt the teachings of the present invention to create other embodiments and applications.

BRIEF DESCRIPTION OF THE DRAWINGS

The exact nature of this invention, as well as its objects and advantages, will become readily apparent from consideration of the following specification as illustrated in the accompanying drawings, in which like reference numerals designate like parts throughout the figures thereof, and wherein.

DETAILED DESCRIPTION

The following description is provided to enable any person skilled in the art to make and use the invention and sets forth the best modes contemplated by the inventor for carrying out the invention. Various modifications, however, will remain readily apparent to those skilled in the art.

Figure 1:
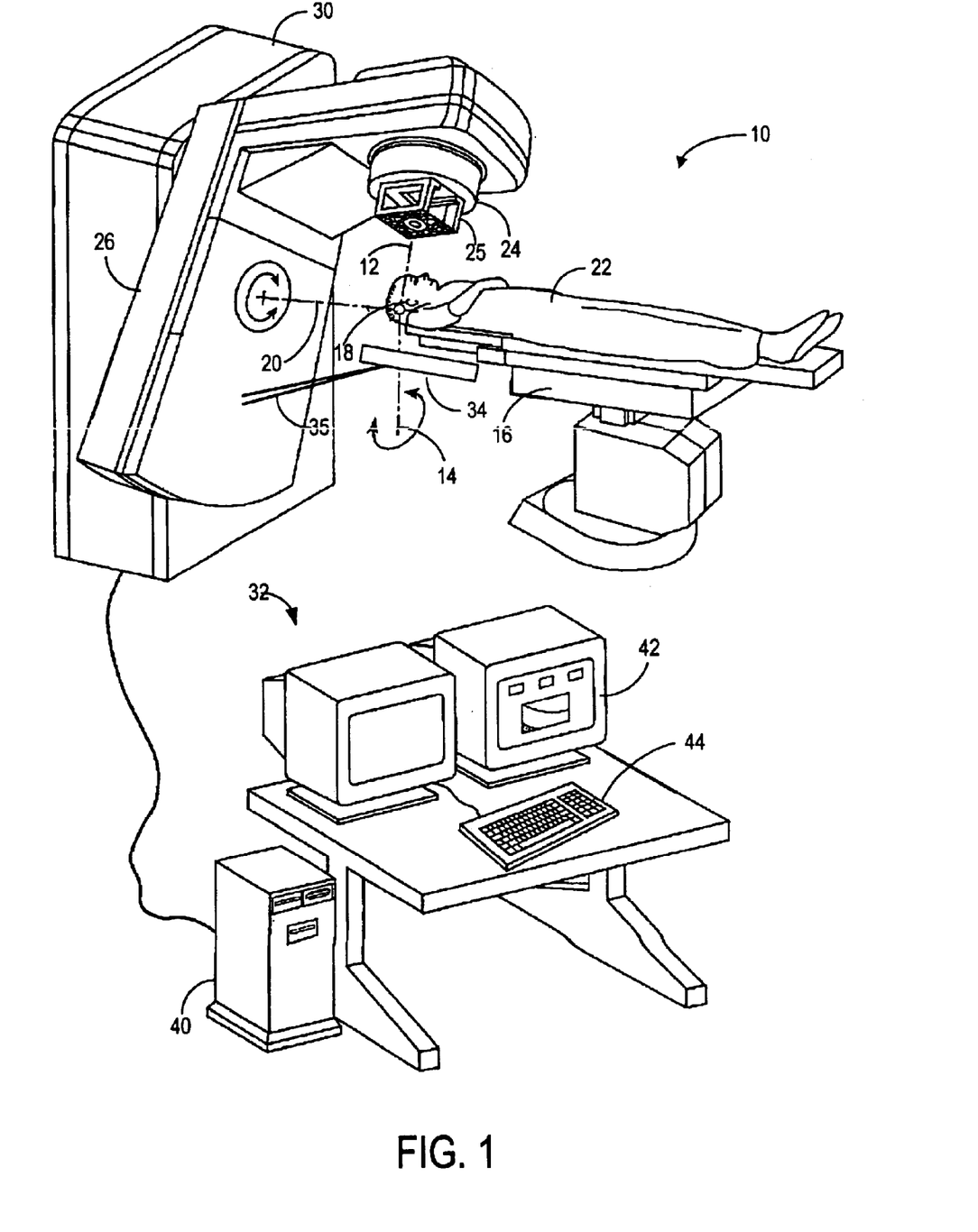
FIG. 1 is diagram illustrating a radiation therapy device.

Turning now to the drawings and, with particular attention to FIG. 1, a radiation therapy device 10 pursuant to embodiments of the present invention is shown. According to one embodiment of the present invention, radiation therapy device 10 includes a beam shielding device (not shown) within a treatment head 24, a control unit in a housing 30 and a treatment unit 32. An accessory tray 25 is mounted to an exterior of treatment head 24. Accessory tray 25, in one embodiment, is configured to receive and securely hold attachments used during the course of treatment planning and treatment (such as, for example, reticles, wedges, or the like).

Radiation therapy device 10 includes a gantry 26 which can be swiveled around a horizontal axis of rotation 20 in the course of a therapeutic treatment. Treatment head 24 is fastened to a projection of the gantry 26. A linear accelerator (not shown) is located inside gantry 26 to generate the high energy radiation required for the therapy. The axis of the radiation bundle emitted from the linear accelerator and the gantry 26 is designated by beam path 12. Electron, photon or any other detectable radiation can be used for the therapy. Embodiments of the present invention permit the controlled delivery of both primary electron and primary photon beams to a treatment zone 18 during the course of a prescribed treatment. Embodiments of the present invention also permit the automated control of elements of radiation therapy device 10 during testing or quality assurance cycles, allowing the verification of a prescribed course of treatment.

During a course of treatment, the radiation beam is trained on treatment zone 18 of an object 22, for example, a patient who is to be treated and whose tumor lies at the isocenter of the gantry rotation. The plates or leaves of the beam shielding device within the treatment head 24 are substantially impervious to the emitted radiation. The collimator leaves or plates are mounted between the radiation source and the patient in order to delimit (conform) the field. Areas of the body, for example, healthy tissue, are therefore subject to as little radiation as possible and preferably to none at all. The plates or leaves are movable such that the distribution of radiation over the field need not be uniform (one region can be given a higher dose than another). Furthermore, the gantry can be rotated so as to allow different beam angles and radiation distributions without having to move the patient.

According to one embodiment of the present invention, several beam shaping devices are used to shape radiation beams directed toward treatment zone 18. In one embodiment, a photon collimator and an electron collimator are provided. Each of these collimators, as will be described further below, may be separately controlled and positioned to shape beams directed at treatment zone 18. According to one embodiment, the photon collimator (not shown in FIG. 1) is contained within treatment head 24 and the electron collimator (not shown in FIG. 1) is removably mounted on accessory tray 25.

According to one embodiment of the present invention, radiation therapy device 10 includes a detector 34 which is used, as will be described further below, to perform portal imaging for both photon treatments and electron treatments. Detector 34 may be attached to gantry 26 via an arm structure 35. In some embodiments, arm structure 35 may be remotely operated by an operator to position detector 34 in a desired position.

Detector 34, in one currently-preferred embodiment, is a flat panel imaging device using solid state amorphous silicon sensors. The RID 1640, offered by PerkinElmer®, Inc. of Fremont Calif., is one suitable device. In one embodiment, the imaging device used as detector 34 is formed with a plurality of detector elements formed in a two dimensional array. In one embodiment, each detector element (or "pixel") in the array is a solid state sensor, such as a solid state amorphous silicon sensor. Operation of detector 34 may result in the capture of a two dimensional image. In one embodiment, computer 40 and detector control 49 operate to control detector 34 to capture an image and map the signal detected by each of the detector elements to a gray scale value, providing a graphical depiction of the captured image. Preferably, the imaging device used as detector 34 has sufficient sensitivity and dynamic range to detect low signals or amounts of photons.

Detector 34 may be attached to gantry 26 via arm structure 35 or in some other manner which allows it to be removably placed under patient 22. In other embodiments, detector 34 may be permanently attached to table 16, or movably attached to table 16 such that it may be selectively moved into imaging position as desired. In some embodiments, detector 34 may be used only to verify electron treatment fields. In other embodiments, detector 34 is used to verify both electron and photon treatment fields.

Radiation therapy device 10 also includes a central treatment processing or control unit 32 which is typically located apart from radiation therapy device 10. Radiation therapy device 10 is normally located in a different room to protect the therapist from radiation. Treatment unit 32 includes a processor 40 in communication with an operator console 42 (including one or more visual display units or monitor) and an input device such as a keyboard 44. Data can be input also through data carriers such as data storage devices or a verification and recording or automatic setup system. More than one control unit 32, processor 40, and/or operator console 42 may be provided to control radiation therapy device 10.

Treatment processing unit 32 is typically operated by a therapist who administers actual delivery of radiation treatment as prescribed by an oncologist. Therapist operates treatment processing unit 32 by using keyboard 44 or other input device. The therapist enters data defining the radiation dose to be delivered to the patient, for example, according to the prescription of the oncologist. The program can also be input via another input device, such as a data storage device. Various data can be displayed before and during the treatment on the screen of operator console 42. According to one embodiment of the present invention, treatment processing unit 32 receives imaging information from detector 34, allowing the radiation therapist to make any necessary pre-treatment beam or positioning adjustments.

Embodiments of the present invention permit the delivery of both primary electron and primary photon beams to treatment zone 18 during the course of a prescribed treatment. Embodiments of the present invention permit the creation and control of both photon and electron radiation beams which closely match the shape and size of treatment zone 18. Further, embodiments of the present invention permit the verification of both electron and photon treatment fields.

Figure 2:
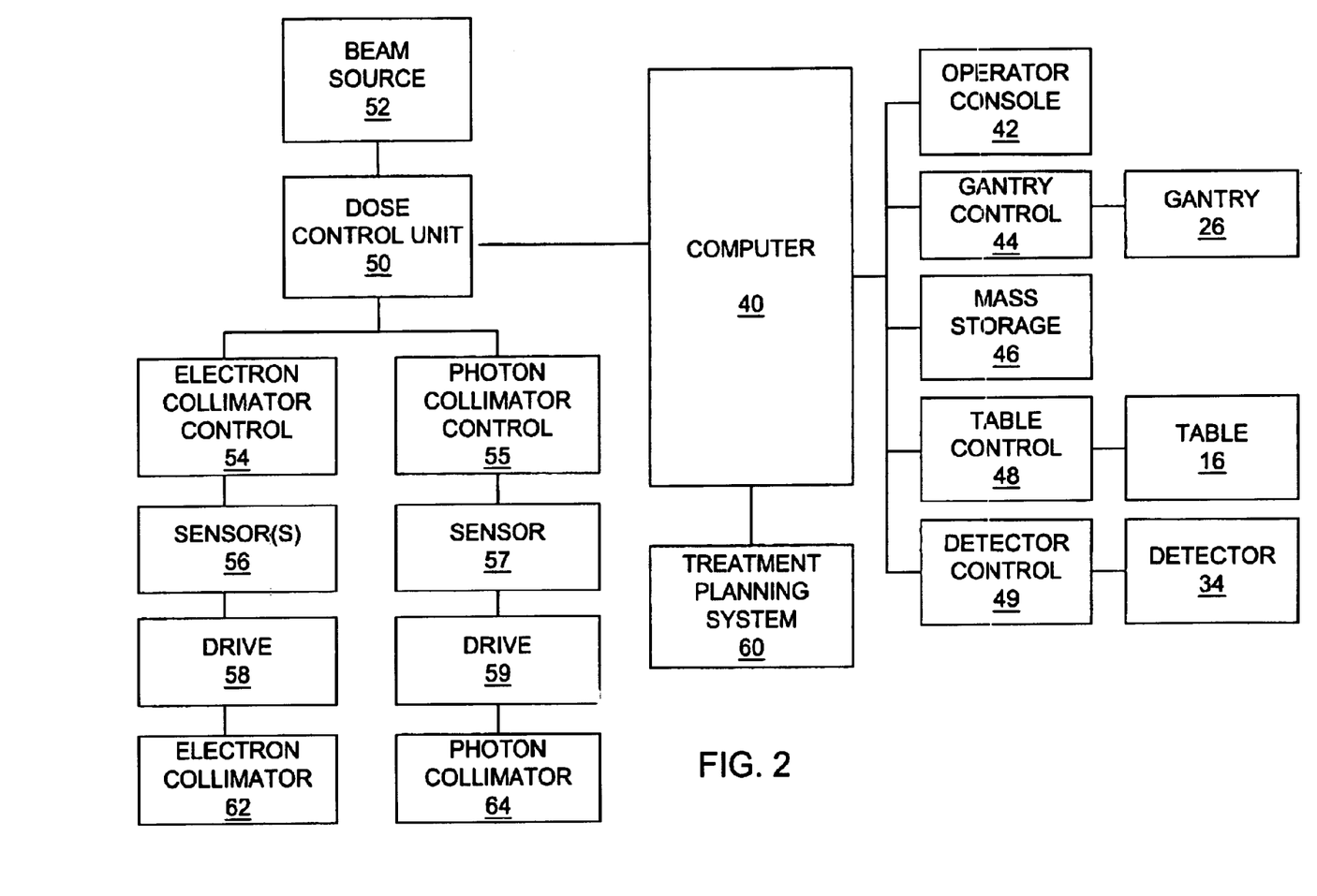
FIG. 2 is a block diagram illustrating portions of the radiation therapy device of FIG. 1 according to one embodiment of the present invention.

Referring now to FIG. 2, a block diagram is shown depicting portions of a radiation therapy device 10 and treatment unit 32 according to one embodiment of the present invention. In particular, treatment delivery elements of a radiation therapy device are shown, which may be configured in radiation therapy device 10 and treatment unit 32 as depicted in FIG. 1. The treatment delivery elements include a computer 40, operatively coupled to an operator console 42 for receiving operator control inputs and for displaying treatment data to an operator. Operator console 42 is typically operated by a radiation therapist who administers the delivery of a radiation treatment as prescribed by an oncologist. Using operator console 42, the radiation therapist enters data that defines the radiation to be delivered to a patient.

Mass storage device 46 stores data used and generated during the operation of the radiation therapy device including, for example, treatment data as defined by an oncologist for a particular patient. This treatment data is generated, for example, using a treatment planning system 60 which may include manual and computerized inputs to determine a beam shape prior to treatment of a patient. Treatment planning system 60 is typically used to define and simulate a beam shape required to deliver an appropriate therapeutic dose of radiation to treatment zone 18.

Data defining the beam shape and treatment are stored, e.g., in mass storage device 46 for use by computer 40 in delivering treatment. According to one embodiment of the present invention, treatment planning may include activities which occur prior to the delivery of the treatment, such as the generation of treatment data defining a photon treatment, an electron treatment, and/or a mixed beam treatment. Embodiments of the present invention permit the use of mixed beam treatments without the need for extended disruptions to install electron applicators or other shielding devices. Further, embodiments of the present invention permit field shaping of electron beams during a treatment in a device which also permits field shaping of photon beams during a treatment. Embodiments of the present invention also permit the verification of photon, electron, and mixed beams.

Mass storage device 46 may also store other information and programs used to operate radiation therapy device 10. For example, mass storage device 46 may store one or more interlock libraries, each defining one or more interlocks to be used in the operation of radiation therapy device 10 in a particular operation mode (e.g., different interlocks may be used depending on whether the treatment uses primary electrons, primary photons, or mixture of primary electrons and primary photons).

Although a single computer 40 is depicted in FIG. 2, those skilled in the art will appreciate that the functions described herein may be accomplished using one or more computing devices operating together or independently. Those skilled in the art will also appreciate that any suitable general purpose or specially programmed computer may be used to achieve the functionality described herein.

Computer 40 is also operatively coupled to various control units including, for example, a gantry control 44 and a table control 48. In operation, computer 40 directs the movement of gantry 26 via gantry control 44 and the movement of table 16 via table control 48. These devices are controlled by computer 40 to place a patient in a proper position to receive treatment from the radiation therapy device. In some embodiments, gantry 26 and/or table 16 may be repositioned during treatment to deliver a prescribed dose of radiation.

According to one embodiment of the present invention, computer 40 is operatively coupled to a detector control 49. Detector control 49 is used to control the operation of detector 34 to perform treatment field verifications pursuant to embodiments of the present invention. Embodiments of the present invention permit the accurate and efficient verification of electron treatment fields, as well as photon and mixed beam fields. The result is a radiation therapy device that allows accurate and verifiable delivery of a wide variety of radiation treatments. In some embodiments, detector control 49 may also be used to control the positioning of detector 34. In other embodiments, detector 34 may be positioned manually. In one embodiment, computer 40 operates detector control 49 prior to delivery of a planned treatment protocol to allow the verification of a treatment field.

According to one embodiment of the present invention, computer 40 and detector control 49 perform processing to enhance or manipulate the image captured by detector 34 (e.g., as described in the co-pending U.S. patent application for "VERIFICATION OF TREATMENT FIELDS" referred to above). As a result, processing performed by computer 40 and detector control 49 may be used to generate a portal image depicting the patient anatomy and the electron collimator field edge.

Computer 40 and detector control 49 may also be used to capture multiple electron fields, each of which may be added to each other to depict a relative display of intensity. In such an application, each of the images are compiled separately. Embodiments of the present invention may also be used to capture photon treatment images immediately subsequent to the capture of electron treatment images, thereby allowing the verification of mixed beam treatments.

Computer 40 is also operatively coupled to a dose control unit 50 which includes a dosimetry controller and which is designed to control a beam source 52 to generate a desired beam achieving desired isodose curves. Beam source 52 may be one or more of, for example, an electron, and/or photon beam source. Beam source 52 may be used to generate radiation beams in any of a number of ways well-known to those skilled in the art. For example, beam source 52 may include a dose control unit 50 used to control a trigger system generating injector trigger signals fed to an electron gun in a linear accelerator (not shown) to produce en electron beam as output. Beam source 52 is typically used to generate a beam of therapeutic radiation directed along an axis (as shown in FIG. 1 as item 12) toward treatment zone 18 on patient 22.

According to one embodiment of the invention, the beam generated by beam source 52 is shaped using one or more collimator assemblies, depending on the type of beam generated. For example, in one embodiment, a photon beam produced by beam source 52 is shaped by manipulating a photon collimator 64, while an electron beam produced by beam source 52 is shaped by manipulating an electron collimator 62. According to one embodiment, photon collimator 64 and electron collimator 62 are multi-leaf collimators having a plurality of individually-movable radiation blocking leaves. The leaves of each such collimator are individually driven by a drive unit 58, 59 and are positioned under the control of electron collimator control 54, photon collimator control 55 and sensor(s) 56 and 57.

Drive units 58, 59 move the leaves of each collimator in and out of the treatment field to create a desired field shape for each type of beam. In one embodiment, where an electron beam is to be generated and primary electrons are to be used in a treatment, photon collimator control 55 operates to retract individual leaves of photon collimator 64, while electron collimator control 54 operates to position individual leaves of electron collimator 62 across the path of the electron beam to generate a desired electron field shape at the isocenter. Similarly, in one embodiment, where a photon beam is to be generated and primary photons are to be used in a treatment, electron collimator control 54 operates to retract individual leaves of electron collimator 62 while photon collimator control 55 operates to position individual leaves of photon collimator 64 across the path of the photon beam to generate a desired photon beam field shape at the isocenter. In other embodiments, both collimators 62, 64 may be controlled in concert during the course of a treatment to generate a desired field shape at the isocenter.

Figure 3:
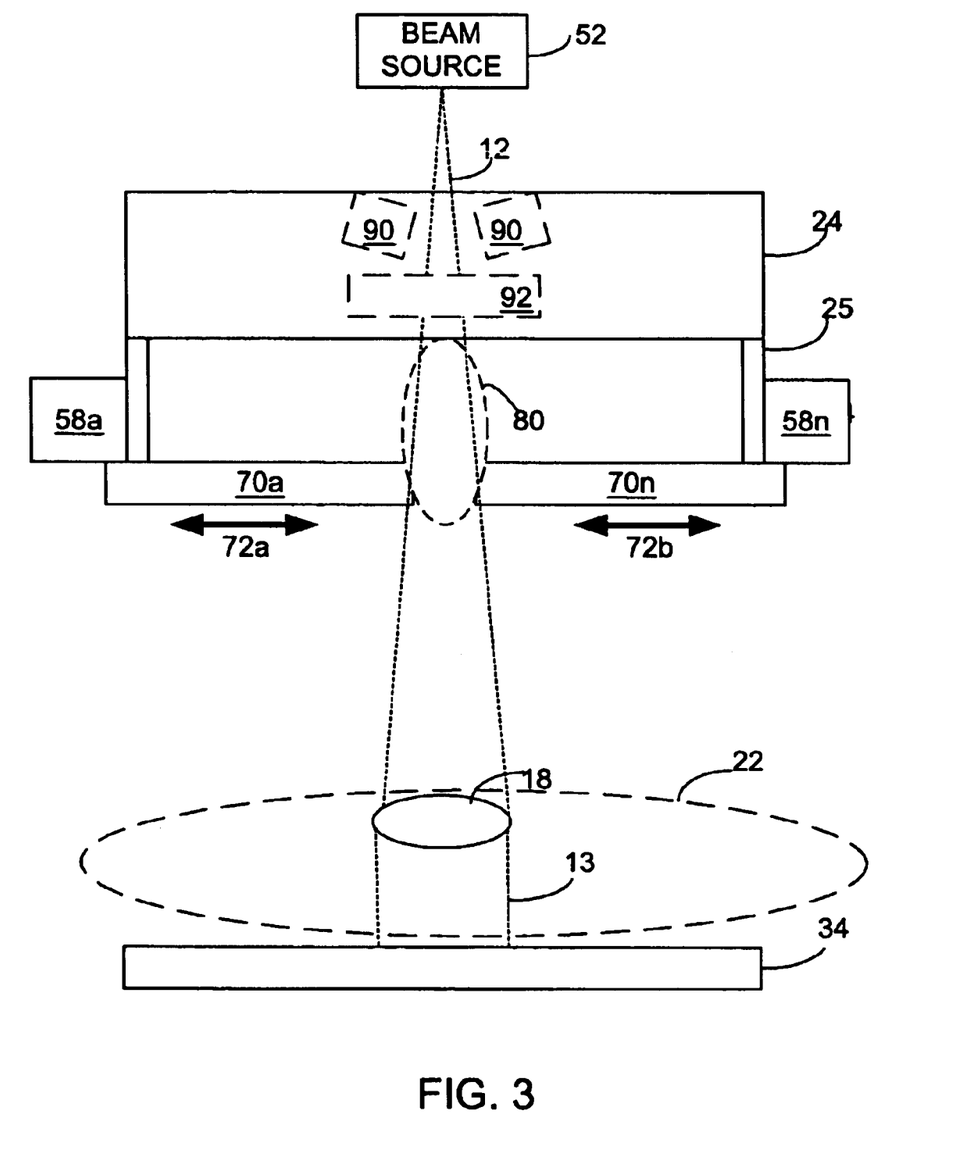
FIG. 3 is a diagram illustrating portions of the radiation therapy device of FIG. 1 according to one embodiment of the present invention.

Referring now to FIG. 3, a perspective view of portions of radiation therapy device 10 is shown. In particular, FIG. 3 depicts portions of treatment head 24 as well as elements along a beam path 12. According to one embodiment of the present invention, treatment head 24 includes an accessory tray 25 or other mounting device positioned between treatment head 24 and treatment area 18. Components of a photon collimator (item 64 of FIG. 2) are shown as collimator blocks 90, 92 in FIG. 3. Collimator blocks 90, 92 are positioned within treatment head 24 and may include a number of individual elements or "leaves" which may be independently controlled to create a desired field shape at the isocenter. Any of a number of known collimators and shaping devices may be used as photon collimator (item 64 of FIG. 2) in conjunction with embodiments of the present invention.

According to one embodiment of the present invention, a separate electron collimator 62 is provided. According to one embodiment of the present invention, components of electron collimator 62 are removably mounted on accessory tray 25, allowing electron collimator 62 to be quickly installed and removed by radiation therapists or other technicians in order to add or remove electron field shaping capabilities to a radiation therapy device. According to one embodiment, individual leaf beds consisting of a number of individual collimator leaves 70*a–n* are mounted on accessory tray 25 such that they can be moved in a direction 72 across beam path 12. In one embodiment, the individual leaves 70*a–n* are formed of radiation attenuating materials. For example, brass or tungsten are currently preferred materials, although other materials with similar radiation attenuating characteristics may be used. In one embodiment, individual leaves 70*a–n* have a width of approximately 1–2 cm. Those skilled in the art will recognize that other shapes and sizes of individual leaves 70*a–n* may be selected to produce different field shapes at treatment zone 18.

Collimator drives 58*a–n* and other control circuitry are also removably mounted on accessory tray 25. In one embodiment, collimator drives 58*a–n* and other control circuitry are mounted on an exterior surface of accessory tray, away from beam path 12, providing greater durability and length of service for the electrical components used to operate electron collimator 62.

According to one embodiment of the present invention, a container 80 (such as a balloon or the like) filled with helium is positioned along a portion of beam path 12 to reduce the amount of free air along beam path 12. In one embodiment, container 80 is removably mounted to accessory tray 25. By replacing some of the air in the air column with helium (or another gas having a low density), the penumbra of the electron beam is reduced, allowing greater control over the shape and effect of the beam at the isocenter. In particular, use of helium along beam path 12 maintains the electron beam spread at a clinically acceptable level by decreasing the number of scattering interactions the electrons experience before they reach treatment zone 18. In operation, a shaped electron field may be delivered to treatment zone 18 by retracting leaves of photon collimator blocks 90, 92, passing the electron beam through helium-filled container 80, and selectively shaping the beam by manipulating electron collimator 62. Multiple fields can thus be delivered to treatment zone 18 during the course of a treatment without manual intervention. Further, embodiments of the present invention support mixed beam treatments by selectively switching between electron and photon beams. According to embodiments of the present invention, manual intervention and equipment set-up is reduced or eliminated.

Applicants have found that mounting components of electron collimator 62 on accessory tray 25 provides several desirable benefits. For example, during most types of treatments, electron collimator 62 provides sufficient patient clearance in all gantry and table positions. Further, electronic components, such as collimator drives 58*a–n*, will enjoy greater longevity because they are positioned away from beam path 12. Additionally, greater accuracy is provided during treatment because the overall swing weight of treatment head 24 and accessory tray 25 are minimized. The inventive configuration also enjoys the advantage of allowing ready removal and replacement of components. Accessory tray 25, in some embodiments, includes one or more accessory slots (not shown) into which components of electron collimator 62 may fit. In some embodiments, components of electron collimator 62 are installed by simply inserting the components into one or more accessory slots of accessory tray 25. As a result, for treatments that require greater clearance (e.g., such as photon treatments of breast cancer, etc.), components of electron collimator 62 may be readily removed, and then re-installed as needed.

Placement of components of electron collimator 62 on accessory tray 25 also serves to reduce the electron penumbra at the isocenter, providing greater accuracy in the delivery of electron treatments. Those skilled in the art will recognize that the electron penumbra can be reduced further by positioning components of electron collimator 62 closer to the isocenter; however, this increases problems with collision. In some embodiments, additional collision detection and avoidance components may be utilized in radiation therapy device 10 to reduce collisions and to allow closer positioning of components of electron collimator 62.

Beam source 52 directs a beam of therapeutic radiation through treatment head and past collimators 62, 64 towards treatment zone 18 on patient 22. According to one embodiment of the present invention, detector 34 may be positioned downstream of patient 22 to perform field verification pursuant to embodiments of the present invention. As described above, embodiments of the present invention permit field verification for both photon and electron beams. When the beam generated by beam source 52 is an electron beam, bremsstrahlung photons are created in treatment head 24. These photons (represented in FIG. 3 as item 13) pass through patient 22 and are detected by detector 34.

Figure 4:
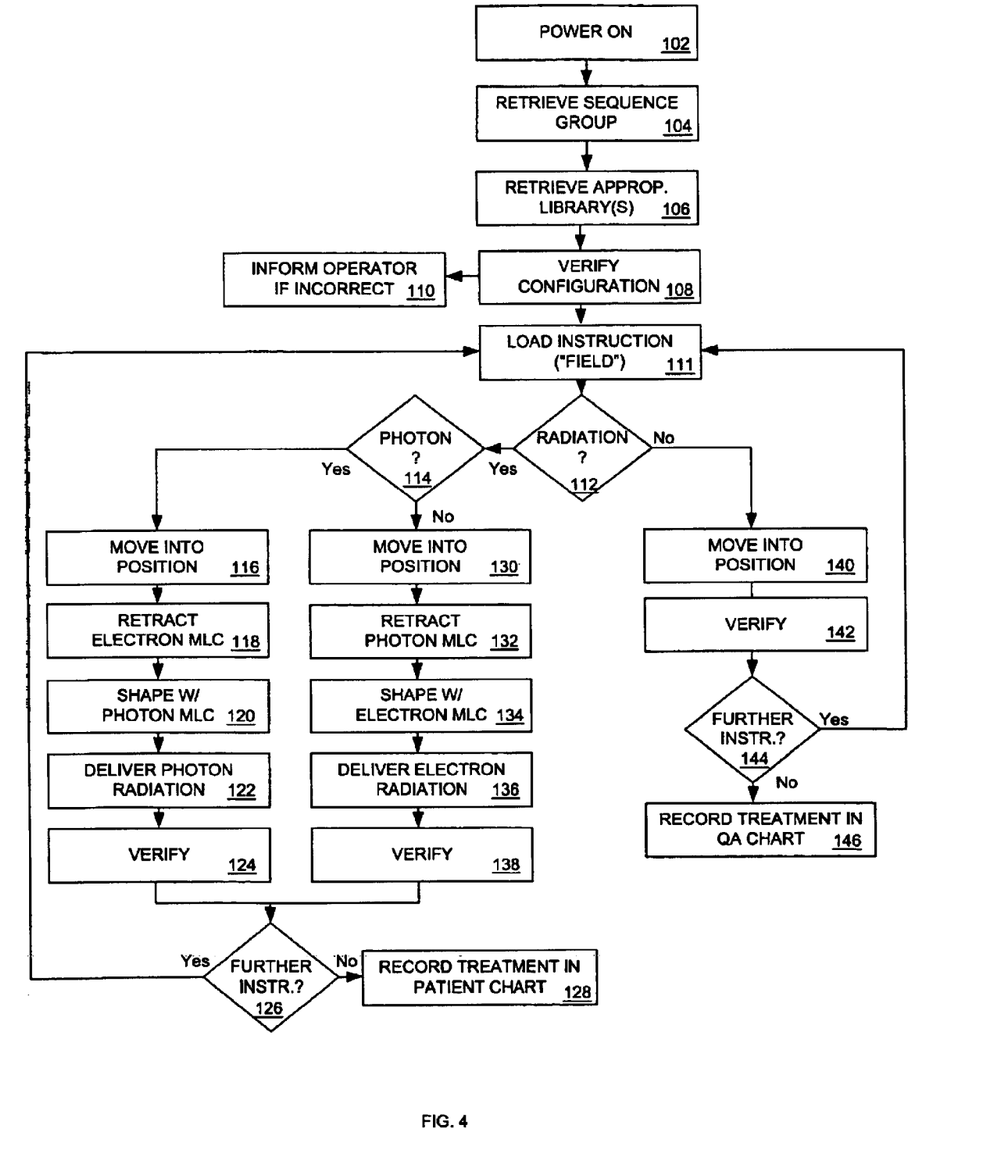
FIG. 4 is a flow diagram illustrating an automated process for the delivery of treatment fields using the radiation therapy device of FIG. 1 according to one embodiment of the present invention.

Referring now to FIG. 4, a flow diagram is shown depicting one embodiment of an automated process 100 for delivering treatment fields using embodiments of the present invention. This processing may be performed under the control of computer program code stored at, or accessible by, computer 40 of treatment processing unit 32. The particular arrangement of elements in the flow chart of FIG. 4 is not meant to imply a fixed order to the steps; embodiments of the present invention can be practiced in any order that is practicable.

Processing begins at 102 where equipment, including radiation therapy device 10 and treatment processing unit 32, are powered on or otherwise enabled for use. Processing continues at 104 where a sequence group is retrieved. According to one embodiment, treatment processing unit 32 may store one or more courses of treatment prescribed for patients by oncologists. These courses of treatment may be stored as one or more sequence groups associated with each patient. This information may be stored at, or accessible to, computer 40. Processing at 104 may involve data entry by a radiation therapist operating operator console 42 to select a particular sequence group. In some embodiments, a particular sequence group is selected by computer 40 once patient information has been selected or entered. According to embodiments of the present invention, each sequence group may be comprised of primary photon treatments, primary electron treatments, or a mixture of both primary photon and primary electron treatments.

Processing continues at 106 where appropriate libraries are retrieved or otherwise identified. Mass storage device 46 (or other devices in communication with computer 40) may store or have accessible to it, one or more interlock, or safety libraries which define permissible control sequences for each treatment type (e.g., different interlocks may be defined for primary photon fields that for primary electron fields). Other libraries and/or data files may also be retrieved at 106, including, for example configuration files defining one or more configurable features of components of radiation therapy device 10. In one embodiment, appropriate libraries and other data files are selected at 106 based on the sequence group retrieved at 104. These libraries will be used to configure and control components of radiation therapy device 10 during delivery of each field of the sequence.

Processing continues at 108 where the configuration of the radiation therapy device 10 is verified. This processing may include polling various components of radiation therapy device 10 to determine if the device is properly configured for the selected sequence group (e.g., if the sequence group defines one or more electron fields to be delivered, processing at 108 may ensure that an electron collimator is installed in an accessory tray of the radiation therapy device 10). If the configuration is not correct, or if there appear to be configuration problems, the operator may be informed at 110 (e.g., by an appropriate display on operator console 42). The operator may be directed to correct the configuration problem before processing proceeds.

Processing continues at 111 where an instruction of the sequence group retrieved at 104 is loaded for processing. Each sequence group may include one or more individual instructions, each defining radiation fields to be delivered by radiation therapy device 10. Each instruction may be separately parsed by computer 40 and used to position components of radiation therapy device 10 to deliver the prescribed field. At 111, the instruction is loaded for processing.

Processing continues at 112 where a determination is made whether radiation is to be applied in the delivery of the field defined in the instruction. In some embodiments, sequencing may include one or more fields which do not require the application of radiation. If the field does not require application of radiation, processing continues to 140 where the instruction is carried out without radiation. In some embodiments, a radiation therapist or operator may select to run a sequence, or individual instructions, without radiation. This selection may be identified at 112. In this manner, embodiments of the present invention may permit a radiation therapist to run through an entire course of treatment without a patient or phantom in place, thereby allowing the radiation therapist to better prepare for an actual treatment.

If radiation is not to be applied, processing continues at 140 where the instruction loaded at 111 is used to configure or position components of radiation therapy device 10 (including, for example, the gantry position, the table position, etc.). For example, the instruction loaded at 111 may include positional instructions for each affected controller. At 140 these positional instructions are forwarded to each affected controller and are used to reorient or position the affected components. Processing at 142 includes receiving feedback from each of the controllers and determining whether the components are properly positioned (e.g., within a predetermined tolerance).

Processing continues at 144 where a determination is made whether any further instructions are contained within the sequence retrieved at 104. If further instructions are in the sequence, processing reverts to 111 and the next instruction is loaded for processing. If no further instructions are in the sequence, processing continues to 146 where the treatment is recorded in a quality assurance chart. In one embodiment, data generated and recorded during the course of a non-clinical or test treatment are stored and recorded in a quality assurance chart associated with the patient's chart. In this manner, radiation therapy device 10 may be operated to run sequence groups for quality assurance testing and measurement before applying the sequence group to the patient.

The data generated during the quality assurance testing may be stored in a manner which does not disrupt, overwrite, or modify data in the patient's chart. In one embodiment, the quality assurance mode may provide the option to rescale the total monitor units of radiation delivered (including the option to set the total monitor units to zero). If a non-zero number of monitor units is selected, embodiments of the present invention redistribute the monitor units to each sequence group and to each field within the group, proportional to the original treatment. Some embodiments of the present invention permit the operator to toggle all gantry and collimator angles and positions to a reference position (e.g., zero) during a quality assurance mode. Applicants have found such a feature useful to measure total dose to a detector placed inside a phantom.

If processing at 112 indicated that radiation is to be applied, processing continues at 114 where a determination of the type of radiation to be applied is made. According to embodiments of the present invention, individual instructions of a sequence group may require the application of different types of radiation (e.g., both primary photons and primary electrons may be delivered in a given sequence). If the loaded instruction requires the application of primary photon radiation, processing continues to 116 where data from the loaded instruction is forwarded to control elements of radiation therapy device 10 to cause the controllers to position their respective components. For example, the loaded instruction may include specific positional information for gantry 26. This positional information may be forwarded from computer 40 to gantry control 44 to cause gantry control 44 to reposition gantry 26 in the desired position for delivery of the field identified by the instruction. Processing at 116 may also include verification that components are properly positioned (e.g., positioned within a desired tolerance).

Once each of the affected components has been moved into position (and verified if appropriate), processing continues to 118 where data of the loaded instruction is used to cause the retraction of electron collimator (element 62 of FIG. 2). Electron collimator 62 may be fully or partially retracted to avoid disruption of the delivery of the desired photon field. Processing at 118 may also include the verification that electron collimator 62 has been properly retracted.

Processing continues at 120 where data of the loaded instruction is used to cause the positioning of photon collimator 64 to form the desired field shape. Processing at 120 may also include the verification that the collimator has been properly positioned.

Processing continues at 122 where radiation therapy device 10 is operated to deliver a dose of photon radiation of the desired intensity and duration (as defined by the instruction loaded at 111). Processing continues at 124 where some verification or adjustment of the dosage applied at 122 occurs. For example, dosimetry devices and techniques may be used to detect, monitor, and measure the amount of radiation delivered at 122. In particular, the radiation delivered at 122 is compared to the prescribed dose defined in the loaded instruction from the sequence group retrieved at 104. In some embodiments, processing at 124 may involve adjusting the dose applied at 122.

Once the prescribed dose for the field has been applied, processing continues at 126 where a determination is made whether any further field(s) are to be delivered (e.g., whether any further instructions of the sequence group remain to be loaded). If so, processing reverts to 111 where the next instruction of the group is loaded.

If processing at 114 indicates that electron radiation, rather than photon radiation, is to be delivered in the field defined by the loaded instruction, processing continues to 130-138 where processing similar to 116-124 occurs, with the exception that photon collimator 64 is partially or fully retracted and electron collimator 62 is moved into a position to properly shape the required field, and a prescribed dose of electron radiation is delivered.

If a determination is made at 126 that no further instructions are to be loaded (i.e., all fields of the sequence group retrieved at 104 have been delivered), processing continues at 128 where data generated and recorded during the course of the treatment are stored and recorded in the patient's chart. In some embodiments, a phantom may be in position during process 100. In such embodiments, data generated during the treatment are recorded and stored in a quality assurance chart rather than the patient's chart.

Those skilled in the art will appreciate that various adaptations and modifications of the just described preferred embodiments can be configured without departing from the scope and spirit of the invention. Although a preferred embodiment utilizing removable electron collimator components has been described, in one embodiment, the electron collimator components may be mounted in a manner that does not facilitate ready removal. Therefore, it is to be understood that, within the scope of the appended claims, the invention may be practiced other than as specifically described herein.

What is claimed is:

1. A method for delivering treatment fields, comprising:

identifying a sequence group comprising instructions defining a plurality of fields, at least one of said plurality of fields comprising a photon field and at least one of said plurality of fields comprising an electron field;

determining a type of radiation to be applied in a first field of said sequence group, said type of radiation selected from primary photon radiation and primary electron radiation;

configuring, based at least in part on said type of radiation, a radiation therapy treatment device to deliver said first field; and delivering said first field.

2. The method of claim 1, further comprising identifying, based at least in part on said type of radiation, at least one interlock library, and wherein said configuring further includes configuring said radiation therapy device based at least in part on said at least one interlock library.

3. The method of claim 1, wherein said configuring includes:

positioning elements of a photon collimator; and positioning elements of an electron collimator.

4. The method of claim 1, wherein said type of radiation is primary photon radiation, and wherein said configuring further comprises:

partially retracting elements of an electron collimator, and positioning elements of a photon collimator to define said field.

5. The method of claim 1, wherein said type of radiation of primary electron radiation, and wherein said configuring further comprises:

partially retracting elements of a photon collimator, and positioning elements of said electron collimator to define said field.

6. The method of claim 1, further comprising:

determining a type of radiation to be applied in a second field of said sequence group, said type of radiation selected from primary photon radiation and primary electron radiation;

configuring, based at least in part on said type of radiation, said radiation therapy treatment device to deliver said second field; and delivering said second field.

7. The method of claim 6, wherein said second field and said first field are different types.

8. The method of claim 1, further comprising:

selecting between a clinical mode and a quality assurance mode; and storing data regarding said treatment sequence in a patient chart if said clinical mode is selected.

9. The method of claim 8, further comprising:

storing data regarding said treatment sequence in a quality assurance chart if said quality assurance mode is selected.

10. A method for automating the delivery of a plurality of treatment fields, comprising:

identifying a sequence group defining said plurality of treatment fields, at least one of said plurality of treatment fields comprising a photon field and at least one of said plurality of treatment fields comprising an electron field;

determining a type of radiation to be applied in a first of said treatment fields, said type of radiation selected from primary photon radiation and primary electron radiation;

configuring, based at least in part on said type of radiation, a radiation therapy treatment device to deliver said first treatment field;

delivering said first treatment field; and repeating said determining, configuring and delivering until each of said plurality of treatment fields of said sequence group have been delivered.

11. A radiation therapy device, comprising:

a beam source, selectively operated to generate a beam having a beam type selected from a primary photon beam and a primary electron beam;

a beam shaping device, selectively operated to shape said beam; and a control system coupled to said beam source and said beam shaping device and operable to identify a treatment sequence group having a plurality of fields, at least one of said plurality of treatment fields comprising a photon field and at least one of said plurality of treatment fields comprising an electron field;

identify a required beam type of each of said plurality of fields; and operate said beam shaping device to shape said beam to deliver each of said plurality of fields.

12. The device of claim 11, wherein said beam shaping device includes an electron collimator and a photon collimator.

13. The device of claim 11, wherein said control system is further operable to capture treatment data during delivery of each of said fields.

14. The device of claim 11, wherein said control system is selectively configured in one of a clinical mode and a test mode.

15. An apparatus for delivering treatment fields, comprising:

means for identifying a sequence group comprising instructions defining a plurality of fields, at least one of said plurality of fields comprising a photon field and at least one of said plurality of fields comprising an electron field;

means for determining a type of radiation to be applied in a first field of said sequence group, said type of radiation selected from primary photon radiation and primary electron radiation;

means for configuring, based at least in part on said type of radiation, a radiation therapy treatment device to deliver said first field; and means for delivering said first field.

16. The apparatus of claim 15, wherein said means for configuring comprise a photon collimator and an electron collimator.

17. A method for testing delivery of radiation fields, comprising:

identifying a sequence group to be tested the sequence group comprising instructions defining a plurality of fields, at least one of said plurality of fields comprising a photon field and at least one of said plurality of fields comprising an electron field;

identifying an instruction of said sequence group, said instruction defining at least a type of radiation to be applied and a configuration of components of a radiation therapy device;

preventing a beam source of said radiation therapy device from generating said radiation;

configuring components of said radiation therapy device as defined by said instruction; and repeating said identifying an instruction, said preventing, and said configuring for each instruction of said sequence group.

* * * * *